United States Patent
Lurz et al.

(10) Patent No.: US 7,530,739 B2
(45) Date of Patent: May 12, 2009

(54) ROBOT-CONTROLLED RECORDING DEVICE

(75) Inventors: Winfried Lurz, Fürth (DE); Manfred Schönborn, Gerhardshofen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/820,243

(22) Filed: Jun. 19, 2007

(65) Prior Publication Data

US 2008/0013690 A1  Jan. 17, 2008

(30) Foreign Application Priority Data

Jun. 20, 2006 (DE) .................. 10 2006 028 327

(51) Int. Cl.
*H05G 1/02* (2006.01)

(52) U.S. Cl. ........................ 378/198; 378/197

(58) Field of Classification Search ............ 378/62, 378/196–198, 167
See application file for complete search history.

(56) References Cited

U.S. PATENT DOCUMENTS

| 4,891,765 | A | 1/1990 | Hatori et al. |
| 6,409,381 | B1 | 6/2002 | Siebenhaar et al. |
| 6,869,217 | B2 | 3/2005 | Rasche et al. |
| 7,319,738 | B2 * | 1/2008 | Lasiuk et al. .................. 378/59 |
| 2003/0091156 | A1 | 5/2003 | Crain et al. |
| 2005/0033149 | A1 | 2/2005 | Strommer et al. |

FOREIGN PATENT DOCUMENTS

| DE | 88 16 311 U1 | 6/1989 |
| DE | 38 06 966 C2 | 10/1992 |
| DE | 199 57 330 A1 | 7/2000 |
| DE | 42 91 619 C2 | 6/2001 |
| EP | 0 642 893 B1 | 3/1995 |
| EP | 1 106 141 A2 | 6/2001 |

* cited by examiner

*Primary Examiner*—Irakli Kiknadze

(57) ABSTRACT

The invention relates to a robot-controlled recording device comprising a robot with a number of axes of movement which are able to be controlled via a robot controller for moving a robotic hand and a recording system fitted to the robotic hand which is able to be moved by the robot for recording data of an object supported on a support unit. The robot controller is connected to an additional drive and controls this for moving the robotic hand synchronized to the axes of movement such that the additional drive would create a relative rotation and/or translation movement between the recording system and the support unit created by the movement of the robotic hand solely by a movement of the support unit with a stationary robotic hand. The drive is however connected not to the support unit but to an encoder for creating a synchronization signal for the recording.

18 Claims, 1 Drawing Sheet

ROBOT-CONTROLLED RECORDING DEVICE

CROSS REFERENCE TO RELATED APPLICATIONS

This application claims priority of German application No. 10 2006 028 327.9 filed Jun. 20, 2006, which is incorporated by reference herein in its entirety.

FIELD OF THE INVENTION

The present invention relates to a robot-controlled recording device, especially for the recording of x-ray image data. The invention also relates to a method for recording data of an object supported on a support device, especially for the recording of x-ray image data, in which a recording system is mounted on a robotic hand having a number of axes of movement and is moved by the robot for recording the data of the object.

BACKGROUND OF THE INVENTION

A main area of application of the recording device as well as of the associated method is the field of x-ray imaging, especially tomographic x-ray imaging. An x-ray apparatus for tomographic x-ray imaging is for example known from DE 199 57 330 A1. This x-ray apparatus features a C-arm, fitted to allow movement to a carriage, on which an x-ray source and an x-ray detector are mounted opposite each other. When this x-ray device is used, in the operating theater for example, the carriage is pushed towards an examination table accommodating the patient and suitably positioned there. For a tomographic x-ray recording the C-arm is moved around the patient for recording a number of two-dimensional x-ray images from different projection directions. In this case an angular area of more than 180° must be covered to enable a three-dimensional reconstruction to be carried out from the two-dimensional x-ray images. The two-dimensional x-ray images are recorded at short intervals synchronized to the movement of the C-arm. This is necessary for a correct image reconstruction.

A principle disadvantage of this type of x-ray device lies in the fact that pushing the x-ray device back and forth as required is cumbersome and demands a high degree of force.

SUMMARY OF THE INVENTION

To counter this disadvantage and to guarantee the best possible access to the patient, the applicant has developed an x-ray device in which a C-arm is coupled to an x-ray source and an x-ray detector mounted opposite the x-ray source on the hand of a robot, which moves this x-ray recording system around the object of interest for recording the two-dimensional x-ray images. However, depending on the type of this movement, this leads to synchronization problems for the recording of the two-dimensional x-ray images. In previously used C-arm x-ray systems the movement of the C-arm is only ever executed with a single motorized axis in each case. This is either the axis of rotation or the orbital axis of the C-arm. This enables a trigger signal to be derived from the movement of this axis, which is used for the synchronization of the x-ray image recording. A correct 3D reconstruction can then be carried out with this synchronization signal or the synchronization pulses and the associated 2D-x-ray imaging system.

With a robot-guided C-arm this type of synchronization is only still possible in a simple manner on rotation of the C-arm around the axis of rotation, since once again with a robot featuring six axes of rotation only one motorized axis can be rotated. On the other hand a movement of all axes of the robot is required for orbital movements of the C-arm, with said axes not moving linearly however. In addition it can occur that individual axes run backwards during such a movement, so that no synchronization to these movement axes is possible.

The object of the present invention consists of specifying a robot-supported recording device as well as a method for recording data of an object supported on a support device which makes possible a correct synchronization of the data recording to the movement of the recording system. The recording device as well as the method should in this case especially make it possible to record tomographic x-ray image data with a recording system which is constructed in a similar manner to a C-arm x-ray system and is guided in an orbital movement by the robot as the images are being recorded.

The object is achieved by the robot-controlled recording device as well as by the method as claimed in the claims. Advantageous embodiments of the recording device as well as of the method are the object of the subclaims or can be taken from the description below as well as from the exemplary embodiment.

The proposed robot-controlled recording device comprises a robot with a number of axes of movement which are able to be controlled via a robot controller for movement of a robotic hand, and a recording system mounted on the robotic hand which is able to be moved by the robot for recording the data of an object supported on a support device. The robot controller is connected to at least one additional drive and controls the latter for a movement of the robotic hand synchronized with the other axes of movement so that the additional drive would create a relative rotational and/or shifting movement created by the movement of the robotic hand between the recording system and the support unit solely by a movement of the support unit with the robotic hand in a stationary position. The drive is however not connected to the support unit, but to an encoder for creating a synchronization signal for the recording of the data.

In the present recording device the robot controller is thus configured or programmed so that in addition to the drives required for the axes of movement of the robot, it also controls an additional drive or an additional axis. For the robot controller this drive represents a further axis of movement of the robot which moves or rotates the support unit for the object. In this case use is made of the fact that movement of the recording system created by the robot relative to the stationary support unit can be simulated by a displacement and/or rotation of the support unit around or along the further axis of rotation relative to a stationary recording system. The additional axis or the additional drive is controlled here synchronized with the other axes of movement as if this movement and/or rotation with the support unit had occurred. This means that this additional axis always runs linearly, independent of the position of the recording system relative to the support unit or to the object. With the present device however not the support unit but an encoder is driven with the additional drive which supplies a synchronization signal, especially trigger pulses, for the recording of the data of the object. Thus movements such as the orbital movements of the C-arm of an x-ray imaging system can be easily executed with the robot-controlled recording device and synchronized without problems.

With the proposed recording device, for a robot-controlled movement around an axis for which the number of axes of movement of the robot would have to be moved, a synchronization signal for the recording system can be derived in a simple manner.

Preferably the robot has at least six axes of rotation. An articulated-arm robot can for example be involved here, as used on production lines in the automobile industry. The robot features a programmable controller, which enables any sequences of movements of the robotic hand to be predetermined and stored. This programmable controller then also allows the synchronized movement of the additional axis or of the additional drive to be implemented.

The recording system can be embodied with the present recording device and also with the associated method both for image recording and also for other types of data recording, for measurement of the object for example. The present device as well as the associated method are especially suitable in this case for applications in which the recording system needs a synchronization or trigger signal for the recording of the data during the movement by the robotic hand.

In the preferred embodiment an x-ray imaging system is used as the recording system, which features an x-ray source and an x-ray detector mounted opposite the x-ray source on a carrier, which is mounted on the robotic hand, for example is coupled to the robotic hand. The carrier is preferably embodied here in the form of a bracket, shaped as a C-arm or U-arm. This carrier can then be moved with the robotic hand for recording a number of x-ray images of the object from different projection directions on an orbital path. This movement corresponds to a rotational movement around an axis which runs at right angles to the plane spanned by the carrier and at right angles to the beam axis of the x-ray beam bundle directed from the x-ray source onto the x-ray detector. This rotational movement, which preferably occurs around what is known as the tool center point, is simultaneously simulated by the robot controller and also by the control of the additional drive as described above. The connection of the additional drive with the encoder thus creates a synchronization signal for a linear rotary movement around this axis of rotation or the tool center point, with which the x-ray imaging system is triggered. The individual two-dimensional x-ray images which are recorded in this case at the various angular positions then have exactly the same angular spacing to each other, so that the three-dimensional reconstruction of a 3D image from these two-dimensional recordings is made possible in a known manner.

In the same way a synchronization signal can obviously also be created for a linear translation movement of the recording system, for example a displacement movement of the x-ray system carrier along the support unit. In this case the additional drive is activated by the robot controller for a displacement movement in this direction, with the additional axis being a translation axis. The combined creation of a synchronization signal for a rotational and a synchronization signal for a translation movement is also possible by appropriate activation of two additional drives or axes. This type of synchronization can for example be required for a movement of the recording system on a spiral path around the object.

BRIEF DESCRIPTION OF THE DRAWINGS

The proposed robot-controlled recording device as well as the associated method will be described below in greater detail with reference to an exemplary embodiment in connection with the drawings without restricting the area of protection specified by the claims. The drawings show:

DETAILED DESCRIPTION OF THE INVENTION

In this exemplary embodiment the robot-controlled recording device and the associated method are explained once again in greater detail with reference to a preferred area of application, the recording of tomographic x-ray image data.

Figure 1:
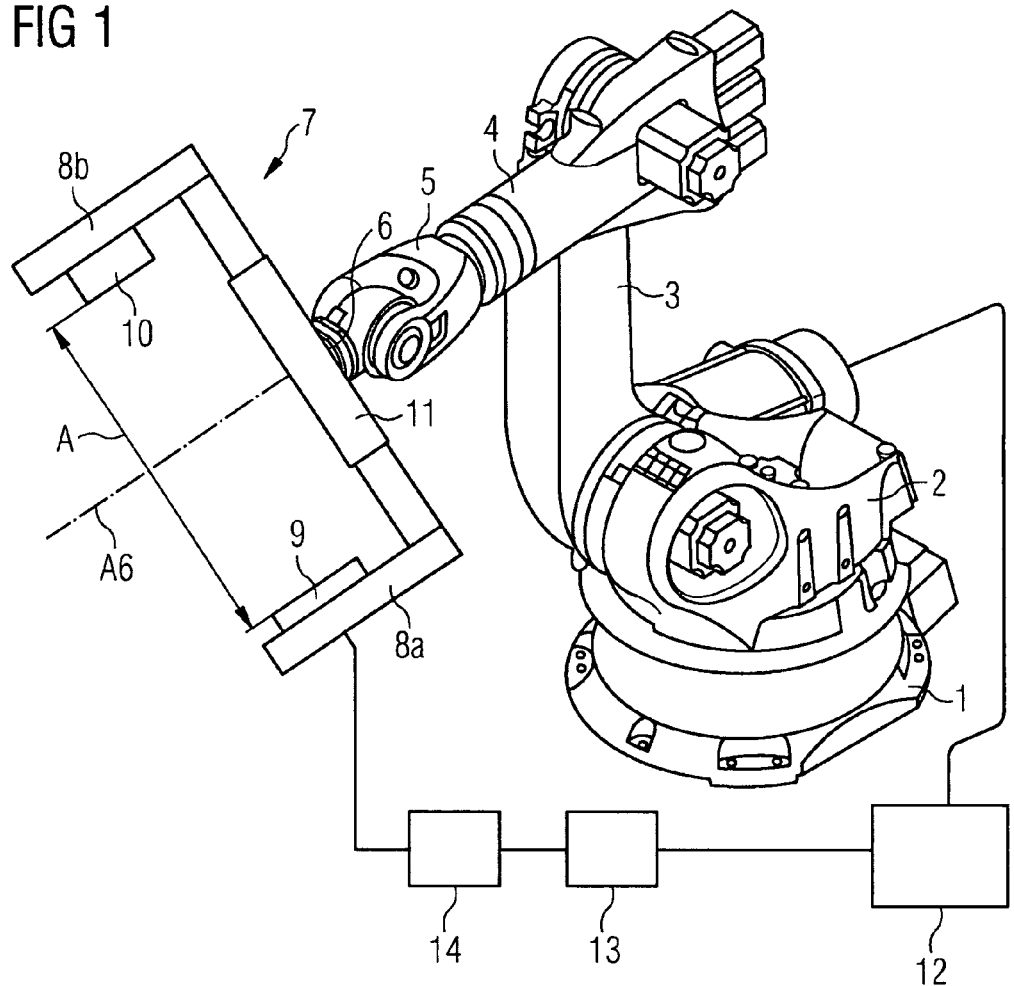
FIG. 1 a perspective view of an inventive recording device.

FIG. 1 here shows a known robot with six axes of rotation. A carousel 2 is mounted to rotate around an axis of rotation A1 on a basic chassis 1, which can be example be fixed to the floor of an operating theater. A swivel arm is fixed to the carousel 2 to allow it to rotate around a second axis of rotation A2. An arm 4 is fixed to the swivel arm 3 to allow it to rotate around a third axis of rotation A3. At the end of the arm 4 a robotic hand 5 is fitted to allow it to rotate around a fourth axis of rotation A4. The hand 5 features an interface 6 for connecting a tool, which can be rotated via the interface 6 around an axis of rotation A6 and is able to be pivoted around a fifth axis of rotation A5 running at right angles to this axis. A carrier generally labeled with the reference symbol 7 is connected to the interface 6 of the hand 5.

The carrier 7 is embodied in the present example as a type of U profile with two opposite legs 8a, 8b. An x-ray detector 9 is fitted to the first leg 8a and an x-ray source 10 is fitted opposite to it on the second leg 8b. The first leg 8a and the second leg 8b can be fitted to allow linear movement in relation to a central element 11 of the carrier 7, so that a distance A between the x-ray detector 9 and the x-ray source 10 can be set.

An additional motor 13 is connected to the robot controller 12 of the robot in the present recording device which is controlled by the robot controller 12. An encoder 14, which then supplies trigger pulses for image recording with the x-ray system comprising x-ray source 10 and x-ray detector 9, is driven by this motor. A 2D x-ray image is recorded with each trigger pulse.

Figure 2:
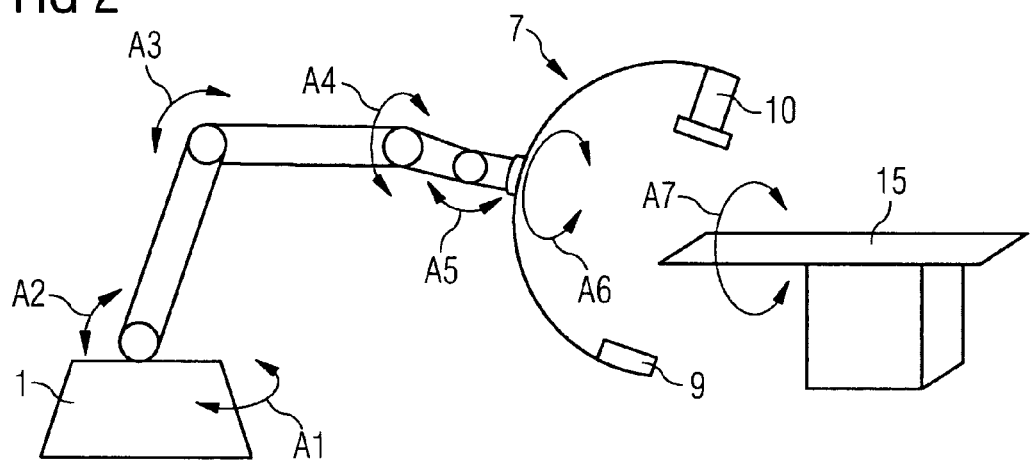
FIG. 2 a schematic diagram of the inventive recording device to explain the method.

The functioning of this robot-controlled recording device is explained in greater detail with reference to FIG. 2, which likewise depicts a schematic diagram of the robot with the six axes of rotation A1 to A6 as well as the carrier 7 with x-ray source 10 and x-ray detector 9. A patient support table 15 is additionally shown in the figure on which a patient (not shown) is supported during x-ray recording.

Initially the carrier 7 is moved with the robot to the patient support table 15 and brought into a predetermined initial position from which x-ray recording can start. The robotic hand moves the carrier 7 for the x-ray recording in the present example for executing an orbital movement around the patient support table 15 or around a patient supported on it. The carrier is moved in this case in a plane around an axis of rotation A7 through the so-called tool center point which lies at right angles to the plane spanned by the carrier 7 and at right angles to the x-ray beam bundle emitted. In this way x-ray detector 9 and x-ray tubes 10 are moved continuously around an angular area of more than 180° around the patient, so that a plurality of two-dimensional x-ray images can be recorded from different angles of projection. The recording of the individual x-ray imaging system is started in this case by trigger pulses which the x-ray imaging system, consisting of x-ray source and x-ray detector, receives from the encoder 14.

The movement of the carrier 7 with the robotic hand is controlled by the robot controller 12. This robot controller likewise controls the additional motor 13 which for the robot controller represents a seventh axis A7 of the robot. This seventh axis is programmed in the robot controller such that it is always moved in synchronization with the x-ray beam and thereby simulates a rotational movement in the tool center point. With the present device and the associated method it is not the rotation of the carrier 7 around the patient table 15 which is used for synchronization of the x-ray imaging system but the seventh axis A7 is controlled as if the patient table 15 were to rotate with a stationary carrier 7 around the axis A7, as shown in FIG. 2. This means that the axis of synchronization, i.e. the seventh axis A7, always runs in a linear direction, regardless of the angle of the carrier 7 to the table. The drive of the encoder 14 with this seventh axis A7 or the associated motor 13 creates trigger pulses which activate the x-ray system for triggering x-ray imaging. These types of pulse can be evaluated by available x-ray systems, as is already currently the case in known C-arm x-ray systems.

After recording the images the robot then moves the carrier 7 with the x-ray system away from the patient support table 15 again, so that the patient is freely accessible to the doctor.

The invention claimed is:

1. A robot-controlled recording device, comprising:
    a robot that moves in a plurality of axes of movement, the robot comprising a robot hand;
    a robot controller that controls a movement of the robot hand;
    a recording system that is mounted on the robotic hand and moved by the robot for recording data of an object supported on a support unit;
    a drive that is connected to the robot controller and controlled by the robot controller for synchronizing the movement of the robotic hand with the axes of movement so that a relative movement between the recording system and the support unit is created by a movement of the support unit with the robotic hand in a stationary position; and
    an encoder that is connected to the drive for creating a synchronization signal to the recording system to record the data of the object.

2. The robot-controlled recording device as claimed in claim 1, wherein the robot is an articulated-arm robot with at least 6 axes of movement.

3. The robot-controlled recording device as claimed in claim 1, wherein the recording device is an x-ray recording device.

4. The robot-controlled recording device as claimed in claim 3, wherein the recording system comprises a carrier comprising an x-ray source and an x-ray detector lying opposite of the x-ray source.

5. The robot-controlled recording device as claimed in claim 4, wherein the carrier is moved by the robot for recording a plurality of x-ray images of the object from a plurality of different projection directions.

6. The robot-controlled recording device as claimed in claim 4, wherein the carrier has a bracket shape.

7. The robot-controlled recording device as claimed in claim 4, wherein the carrier is rotated by the robot in a plane around an axis that is perpendicular to the plane and perpendicular to a beam axis of an x-ray beam bundle directed from the x-ray source to the x-ray detector.

8. The robot-controlled recording device as claimed in claim 1, wherein the relative movement between the recording system and the support unit is a rotational or translational movement.

9. The robot-controlled recording device as claimed in claim 1, wherein the relative movement between the recording system and the support unit is a simulated movement.

10. A method for recording data of an object supported on a support unit, comprising:
    mounting a recording system on a robotic hand of a robot having a plurality of axes of movement;
    synchronizedly moving the robotic hand with the axes of movement so that a relative movement between the recording system and the support unit is created by a movement of the support unit with the robotic hand in a stationary position; and
    supplying a synchronization signal for the recording system to record the data of the object.

11. The method as claimed in claim 10, wherein the robot is an articulated-arm robot with at least 6 axes of movement.

12. The method as claimed in claim 10, wherein the recording system comprises a carrier comprising an x-ray source and an x-ray detector lying opposite of the x-ray source.

13. The method as claimed in claim 12, wherein the carrier is moved by the robot for recording a plurality of x-ray images of the object from a plurality of different projection directions.

14. The method as claimed in claim 12, wherein the carrier is rotated by the robot in a plane around an axis that is perpendicular to the plane and perpendicular to a beam axis of an x-ray beam bundle directed from the x-ray source onto the x-ray detector.

15. The method as claimed in claim 12, wherein the carrier is guided by the robot in recording the x-ray images on a spiral path around the object.

16. The method as claimed in claim 10, wherein the relative movement between the recording system and the support unit is a rotational or translational movement.

17. The method as claimed in claim 10, wherein the relative movement between the recording system and the support unit is simulated by a drive.

18. The method as claimed in claim 17, wherein the drive is connected to an encoder that creates the synchronization signal.

* * * * *